US011521718B2

(12) United States Patent
Tapadar et al.

(10) Patent No.: US 11,521,718 B2
(45) Date of Patent: Dec. 6, 2022

(54) MOBILE APPLICATION FOR MEDICATION REMINDERS

(71) Applicant: CERNER INNOVATION, INC., North Kansas City, MO (US)

(72) Inventors: Soumen Tapadar, Bangalore (IN); Kiran Chornoor, Bangalore (IN); Prashant Pagi, Bangalore (IN)

(73) Assignee: CERNER INNOVATION, INC., North Kansas City, MO (US)

( * ) Notice: Subject to any disclaimer, the term of this patent is extended or adjusted under 35 U.S.C. 154(b) by 185 days.

(21) Appl. No.: 16/902,987

(22) Filed: Jun. 16, 2020

(65) Prior Publication Data

US 2020/0312435 A1 Oct. 1, 2020

Related U.S. Application Data

(63) Continuation of application No. 15/099,231, filed on Apr. 14, 2016, now Pat. No. 10,740,439.

(51) Int. Cl.
*G16H 10/60* (2018.01)
*G16H 20/10* (2018.01)
*G16H 40/67* (2018.01)

(52) U.S. Cl.
CPC ............. *G16H 10/60* (2018.01); *G16H 20/10* (2018.01); *G16H 40/67* (2018.01)

(58) Field of Classification Search
CPC .... G06F 19/3456; G16H 10/60; G16H 20/60; G16H 20/70; G16H 20/90
See application file for complete search history.

(56) References Cited

U.S. PATENT DOCUMENTS

| 8,706,523 | B2 | 4/2014 | Kulawiec et al. |
| 2010/0159978 | A1 | 6/2010 | Sierawski |
| 2012/0101847 | A1* | 4/2012 | Johnson ................. G06Q 10/00 705/3 |
| 2016/0042128 | A1 | 2/2016 | Krigsvold et al. |
| 2017/0193186 | A1 | 7/2017 | Tapadar et al. |

OTHER PUBLICATIONS

Montuno_Software_Website.pdf, Dosecast, Montuno Software, October (Year: 2014) via https://archive.org/on Aug. 8, 2018.*
"Montuno Software", Dosecast Mobile Phone Application, Accessed on Oct. 8, 2014, 5 pages.

* cited by examiner

*Primary Examiner* — Michael Tomaszewski
*Assistant Examiner* — Mohmad Muqueeth
(74) *Attorney, Agent, or Firm* — Shook, Hardy & Bacon L.L.P.

(57) ABSTRACT

Methods, systems, and computer-readable media are provided for computer based healthcare information to automatically provide reminders to a patient to take prescription medications at the appropriate times on the patient's mobile device. The patient enters a medical record number (MRN) into the mobile device and this information is communicated to the patient's electronic medical record. The user device receives the prescription information for the MRN from the patient's electronic medical record. Utilizing the prescription information on the user's device, the user can view and set reminders to take the medication directly from the patient's mobile device.

20 Claims, 16 Drawing Sheets

| PRESCRIPTIONS | |
|---|---|
| 30/04/15 | |
| CODALINE | |
| 10/04/15 | |

| ASPIRIN | |
|---|---|
| STRENGTH DOSE | 500 |
| STRENGTH DOSE UNIT | MG |
| DRUG FORM | TAB |
| ADMINISTRATION ROUTE | ORAL |
| FREQUENCY | ONCE |
| DESCRIPTION | FOR PAIN |

ASPIRIN

*FIG. 12.*

MOBILE APPLICATION FOR MEDICATION REMINDERS

CROSS-REFERENCE TO RELATED APPLICATION

This application claims the benefit of U.S. Pat. No. 10,740,439 B2, filed Apr. 14, 2016, entitled "Mobile Application for Medication Reminders", the disclosure of which is incorporated herein by reference in its entirety.

BACKGROUND

Many readmissions to hospitals and clinics occur because patients are not compliant with taking prescribed medications. Patients often forget to take prescribed medicines on time. Additionally, mistakes can be made by patients or caretakers in properly administering the single or multiple medications at home at the right time.

There are medication reminder programs available for reminding patients about medication to be taken on time but all these programs require a manual set up of reminders by keying information's like medication name, dose, drug form, admiration route, frequency, start and stop date time. This can be time consuming activity and can lead to wrong input of information resulting in reminding a patient to take a wrong medication and/or at wrong time.

SUMMARY

The mobile application described provides patient with continuity of care post discharge by facilitating the receipt of latest prescription from an electronic medical record database, such as Cerner Millennium database, by sending MRN (Medical Record Number) as requested. The information received at the user device from the patient's electronic medical record includes the medications prescribed along with details that are required to set reminders for the patient to take the medication. The consumer of the application can have look at each medication detail and set reminder for each one of them or collectively set reminder for all medications by single touch on 'Set Reminder' icon, this action sets the reminder in an alarm manager component. The reminder can also be removed from the alarm manager component by clicking on the Alert icon. Thus, the availability of information required to set reminder eliminates even the remote possibility of making mistakes as compared to manually input of information. The application users a connection with internet through Wi-Fi or mobile data.

Hospitals/clinics that use an electronic medical record database, such as Cerner Millennium Solutions like Power-Orders, to prescribe prescriptions to patient during discharge process can also make sure the continuity of care post discharge by sending the prescription details to patient on demand using CareRemind application. Thus adding value to the services provided to Hospitals/clinics and its patients.

An electronic medical record database, such as Cerner Millennium database, will have the prescriptions ordered by physician for the patients. The user needs to provide the MRN via a user device which will be sent to the database. The database will send the latest prescription for the MRN as a message back to the user device. The user is notified about the message. The details can be viewed and reminder can be set. The application then notifies the user with the reminder at scheduled date and time which the user acknowledges by taking or skipping the medication. All the acknowledgment are stored and maintained as log which the user can view.

The claimed solution is necessarily rooted in computerized electronic medical record technology in order to overcome a problem specifically arising in the realm of computer healthcare information networks, and the claims address the problem of efficiently and correctly providing medication information and reminders to a patient on the patient's mobile device. If adhering to the routine, conventional function of setting medication reminders, a patient would manually enter, such as typing in, each medication and medication information and manually set a reminder on the user's device. This can cause delay and for the incorrect information to be entered.

The claimed invention overcomes the limitations of current computer healthcare information technology and provides other benefits that will become clear to those skilled in the art from the foregoing description.

The claimed system and method of the present application represents a new paradigm of providing medication information and reminders on patient's mobile device. Not only does the claimed invention easily provide medication information and reminders to a patient without manual entry but it also prevents errors in entry of the information and saves the user significant time. Users of electronic medical records or electronic health records utilizing the claimed invention will notice increased performance of their EMR or EHR, increased retrieval of the medication information from storage, fewer user steps to utilize the EMR and user access to the medication information. Furthermore, anything that reduces the number of "clicks" or entries a computer or mobile device user has to make in an EMR or EHR or to enter medication reminders results in reducing the memory utilization, CPU cycles, number of operations that need to be performed by the computer, and power consumption. The resulting cost savings and operational efficiencies of a computer electronic medical record magnify the potential benefits of this technology.

BRIEF DESCRIPTION OF THE DRAWINGS

FIGS. 4-19 are graphical user interface depictions of user flow to set up medication reminders on a user device in accordance with embodiments of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-readable media for a system and method for mobile device users to communicate with an electronic medical or health record and to efficiently and simply set up medication reminders on their mobile device without having to manually input information into their mobile device. The user's mobile device communicates the medical record number (MRN) as request to an electronic medical record service, such as Cerner Millennium database, and the database communicates the latest prescription information for the user in response to the request. On receiving the prescription message back in mobile, the user can review detailed information regarding the medication and set the reminder by single touch or click on the set reminder icon. A user can also set reminders for all medication based on prescription date.

Figure 1:
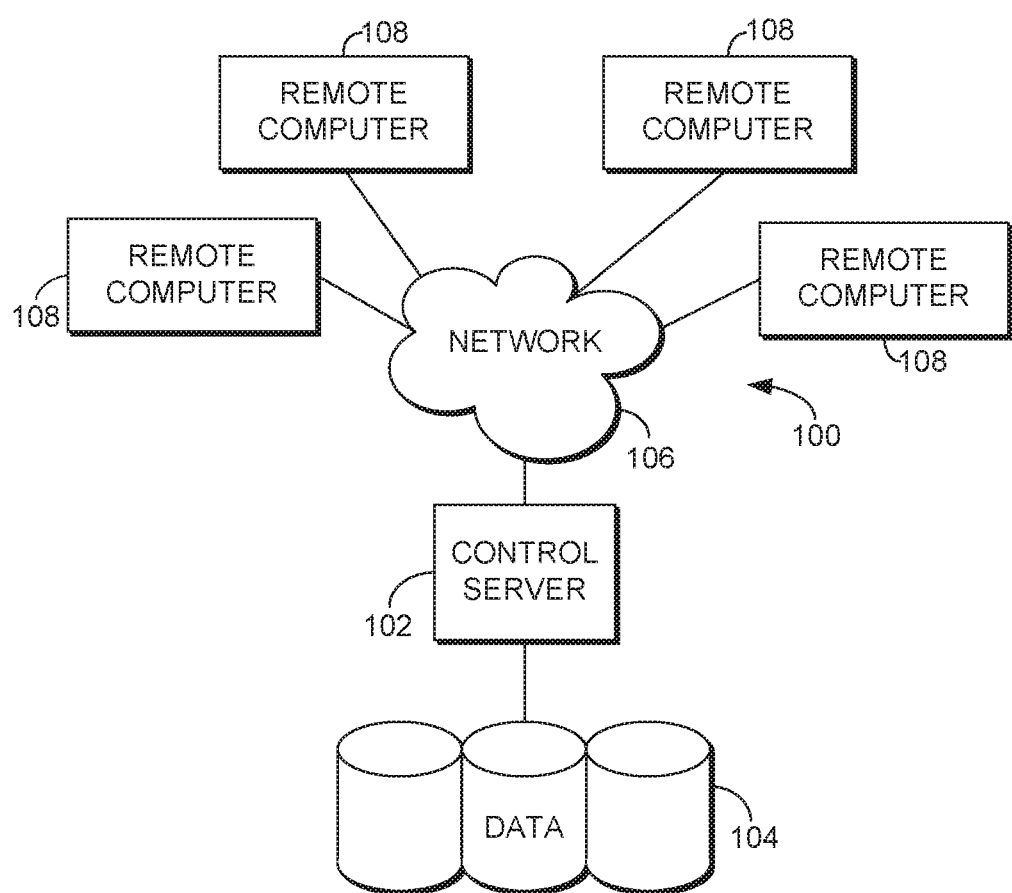
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention is a special computing system that can leverage well-known computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
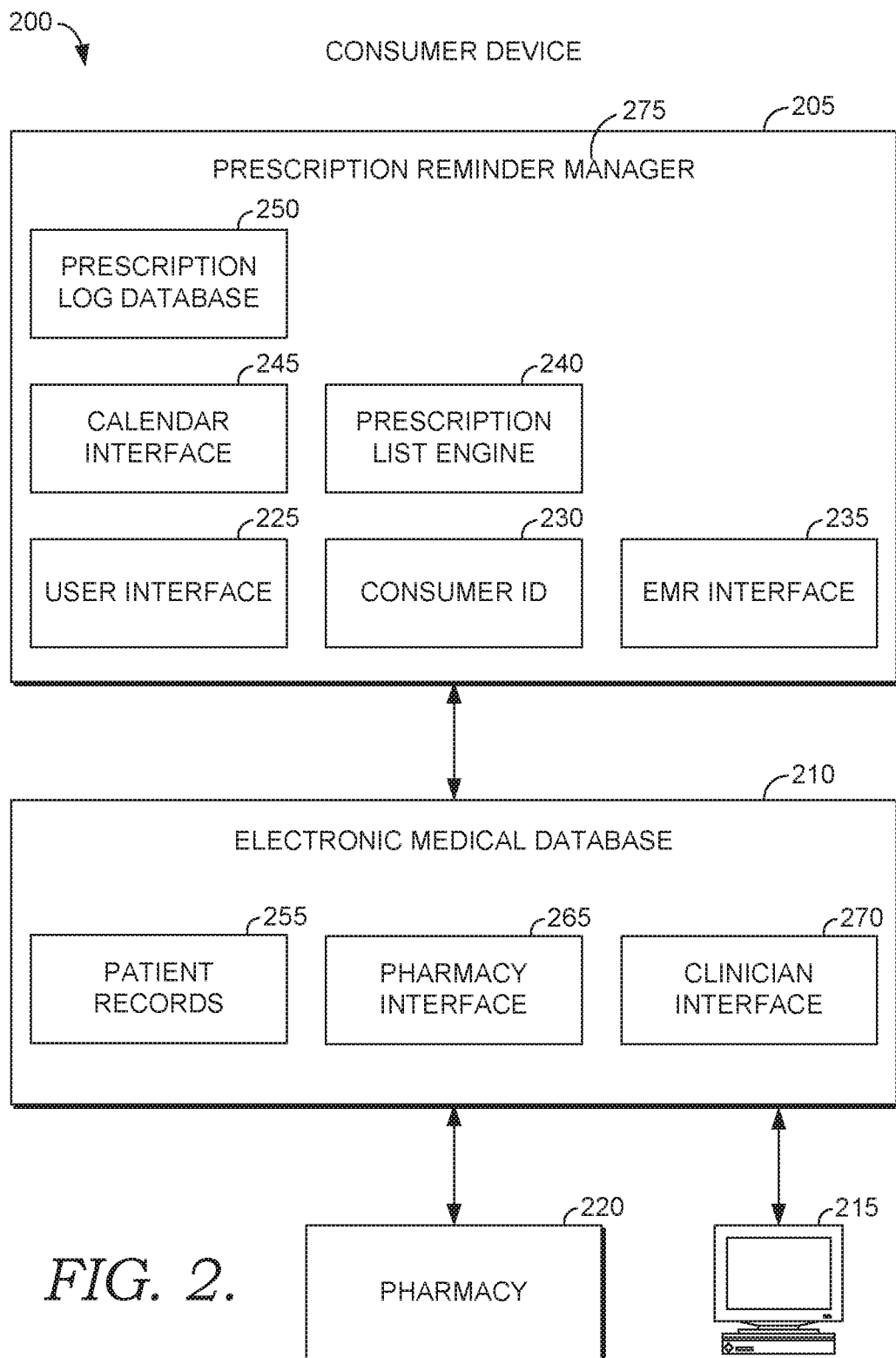
FIG. 2 is an exemplary system architecture suitable to implement embodiments of the present invention.

In an embodiment exhibited by FIG. 2, the processing duties are split among several computing systems. The data store 210 may be implemented through a database system and may be an electronic medical record or electronic health record. The internet serves as a communications link to consumer mobile devices. The tasks performed by the processor utilize a variety of computer technology. In one embodiment, the technology can be divided into three tiers, web server, application server and database server. Each tier is comprised of a number of system layers as described below.

Prescription Reminder Manager

Prescription reminder manager 275 is the control center for consumers, such as patients or family members. Prescription reminder manager 275 resides on a personal computing device or mobile device 205 (such a smart phone) of the consumer. Furthermore, consumer manager 275 has a calendar interface 245 with device 205 such that manager 275 can receive information from the Alarm Manager component residing or connected to device 205.

The prescription reminder manager 275 allows the consumer to communicate with the patient's electronic medical records 210 via a network. The patient or patient representative may initiate request for receiving medication information from the device 205 via user interface 225. The patient identification 230 (Medical Record Number) can be transmitted to an EMR via the EMR interface 235 such that the correct EMR for the patient is utilized.

The prescription reminder manager 275 maintains a user interface 225 with the consumer, patient identification 230 and an API layer between the patient's electronic medical record 210 and the prescription reminder manager 275.

The prescription reminder manager 275 is able to maintain additional patient information such as prescription information for the patient maintained by the prescription list engine 240. The device 205 having the prescription reminder manager 275 has access to AlarmManager, component which is supported on android smart phones, or personal computers. Prescription reminder manager 275 user interface for providing the consumer with a prescription list 240 (discussed in detail below) and information regarding the consumer's medications. A consumer can access known medication information via an interface 225 displayed by the prescription reminder manager 275 on the consumer's smart phone or personal computer 205.

Prescription Reminder Manager

Prescription Reminder Manager 275 (CareRemind) is comprised of subcomponents including user interface 225, Patient identification 230, electronic medical record interface 235, calendar interface 245, prescription list engine 240 and prescription log database 250. It will be appreciated that some or all of subcomponents of prescription reminder manager 275 may be accessed via a network and reside on or more devices remote to consumer device 205. Prescription reminder manager 275 is configured to be used by a consumer, such as a patient, to configure reminders for the patient to take medication as prescribed.

The prescription reminder manager 275 is also in directly or indirectly in communication with one or more electronic medical record databases 210.

User Interface 225

User interface 225 is in communication with prescription reminder manager 275. Prescription reminder manager 275 communicates patient identification 230 (MRN) to EMR 210. User Interface 225 receives MRN as input by the consumer using device 205. User interface 225 communicates and displays medication information and medication reminders generated by the prescription list engine 240.

EMR Interface

Electronic Medical Database 210 is in communication with prescription reminder manager 275 via EMR interface 235. Electronic Medical Database 210 receives the MRN number entered by the user from prescription reminder 275 of device 205. Electronic Medical Database 210 accesses patient records 255 to obtain medication information for the MRN number. Electronic Medical Database 210 then communicates the information via the EMR interface 235 to prescription reminder manager 275 such that the medication information can be provided to the consumer via user interface 225 of device 205.

Prescription List Engine

The prescription list engine then maintains a list of the patient's prescription received from the Electronic Medical Database 210 and arranges the medications according to date prescribed for display to the user. For example, medication attributes include:

Name of the medication including brand name, generic name, chemical name.

Route that the medication is to be administered (e.g., oral administration, nasal administration, ocular administration)

Frequency refers to how often the medication is to be administered to the patient (e.g., once a day, every 4 hours, as needed).

Length refers to how long the medication is to be administered or prescription should last (e.g., 10 days, 12 hours)

Dosage is the amount and strength of the medication that is to be administered (e.g., 2 pills, 2 drops, 5 cc)

Special instructions provided by the clinician such as "take with food, take at night."

Date Prescribed is the date the medication was prescribed.

Prescribing Clinician is the name, address, clinician identifier and DEA number if needed.

Pharmacy fulfilling medication order is the name, pharmacy identifier that has filled the prescription.

Codes and coding information associated with the medication and the above information.

Information regarding physical characteristic of the medication including color, size, markings and textual codes etched on the medication.

Information for each medication such as drug interactions, adverse events and black box warnings.

Prescription list engine 240 leverages information received from the patient record to maintain a running list of medications and associated medication information for the patient associated with the MRNs entered. For example, when consumer uses a first MRN, the MRN is transmitted, decoded and matched by the electronic medical record database 210. Medication associated with the MRN and related information is maintained in in the prescription list engine. The following example, has one medication associated with the MRN entered on the user device and is added to a medication list using prescription list engine 240. However, it will be appreciated there may be multiple medications and associated medications associated with a single MRN, and the medications and associated information is maintained by the prescription reminder manager 275 under a band level for the MRN (and date prescribed). Medication name followed by 'Set Reminder' icon is displayed under the band level.

John Doe Medication List

MRN 12345

Medication 1

On long press over the medication name the attributes will be displayed as described under 0037.

Based on the medication list, if the user requests a reminder for medication 1 (as discussed in more detail below with respect to FIGS. 4-19), the prescription list engine 240 creates reminder requests for the medication and the start date and time for medication. For example, if the user requests a reminder for amoxicillin to start at 10:00 am on Feb. 2, 2016, the prescription list engine would generate reminder requests for the amoxicillin at 10:00 am, 6:00 pm and 2 a.m. for the amoxicillin for each of 10 days starting on Feb. 2, 2016. These reminder requests are communicated to the user device's Alarm Manager component via calendar interface 245. The requests are logged by the Alarm Manager component. When it is time for a reminder, the Alarm Manager component communicates the reminder to the prescription list engine 240 via calendar interface and the prescription reminder manager 275 displays the reminder using the user interface 225. The reminder may also be accompanied by an audible alarm, buzzing and flashing lights depending on the user's preference.

Prescription Log Database

After the prescription list engine displays the reminder to the user via user interface 225, the user can select to mark the medication as 'taken' or 'skipped'. All of the user acknowledgements are stored and maintained by the prescription log database 250 of prescription reminder manager 275 as a log. The log is viewable by the user by selecting to view the log for a medication (as shown below in FIG. 19). The user can navigate through the dates for the medication using the navigation buttons to navigate dates backward and forward. The information is displayed in the log includes date of prescription, the MRN, followed by medication name followed by time when the notification was acknowledge as taken or skipped. In one embodiment, the log can be provided by the user to an authorized third party.

Electronic Medical Record Database

Electronic Medical Record Database 210 is computer store containing healthcare information for individual patients. EMR 210 includes an electronic version of patient records including information for the patient, such as medication and infusion orders, tasks, images, examination reports, testing and lab results, medical history, and prescription information including medical record number (MRN). EMR 210 contains the standard medical and clinical data gathered in a provider's office. An EMR 210 is a digital or computerized version of a paper chart that contains all of a patient's medical history. In the embodiments of the present invention, the patient identifier 230 is stored in the EMR for the individual patient. Additional, medication names, dosage, route and frequency are stored in the patient's EMR associated with a medical record number.

EMR 210 is also in communication via clinician interface 270 and pharmacy interface 265 with one or more clinician devices 215 and pharmacy applications 220. The clinician inputs information for the patient via clinician device which is communicated to the EMR via a network. The pharmacy application also contains information regarding the prescription for the patient. Information from the pharmacy filling the medication(s) can be included in the medical record information (such as pharmacy name, phone number and link to electronically refill medication.)

System Flow

The prescription reminder manager acts as a clearinghouse for all medications for patient to provide a patient with a quick and accurate picture of their medications. The system maintains a real-time interface with patient/consumer and generating medication lists for access by the patient and generating reminders for the patient to take his or her medications. The flow chart of FIG. 3 shows how the distinctive feature which provides user with the facility to send request for latest prescription, set the reminder in mobile and elementary feature which reminds user about the medication to be taken, which is acknowledged by user and can be viewed as log.

Figure 3:
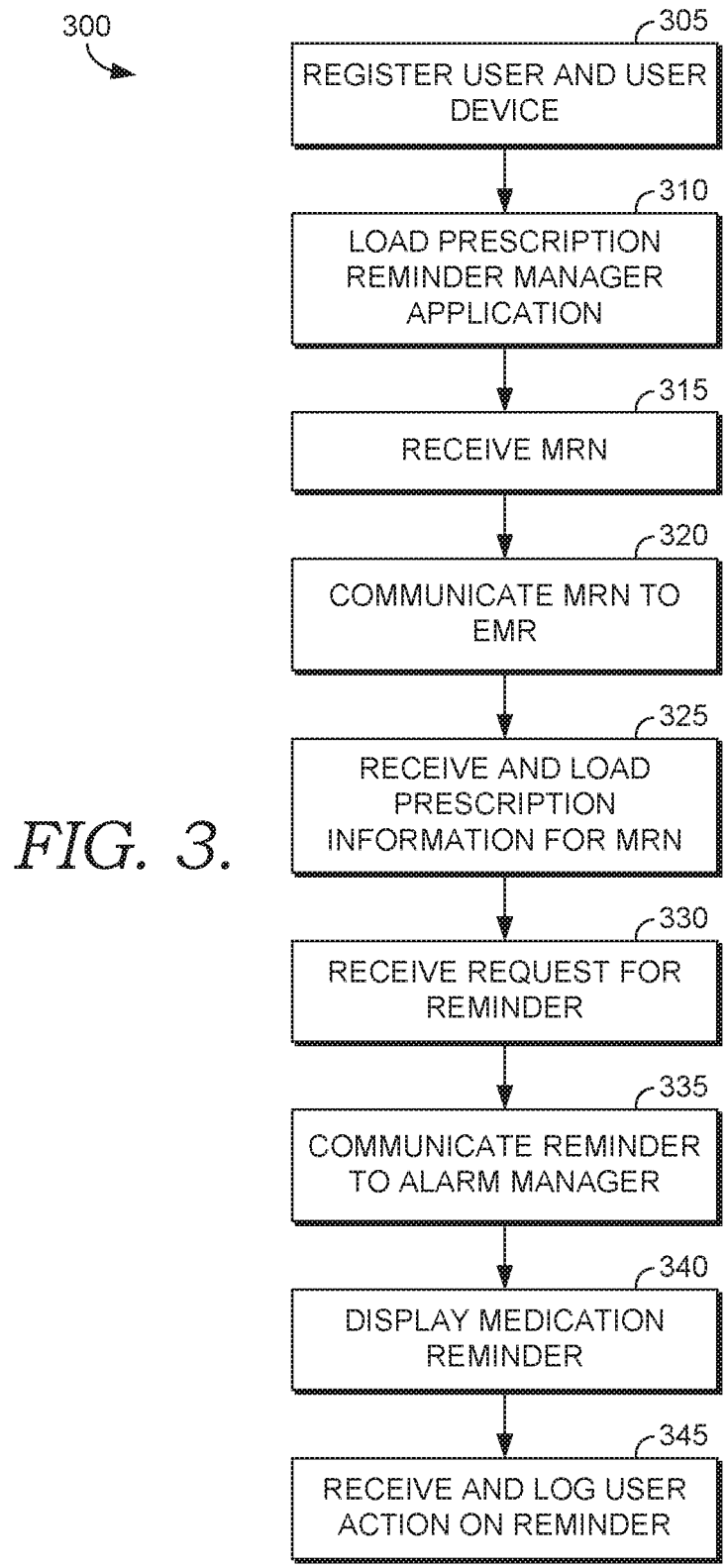
FIG. 3 is a flow diagram depicting embodiments of the present invention.

Referring to FIG. 3, the system flow 300 of the prescription reminder manager application is depicted. The user is typically registered along with the mobile device number at the clinic/facility/hospital during the visit at 305. The consumer (typically the patient) loads to prescription reminder manager application at step 310. This activation is typically accomplished by logging into prescription reminder manager application by the consumer.

Consumer enters an MRN number that they have received during registration or upon discharge from a hospital or clinic. The prescription reminder manager transmits MRN to the electronic medical record database at 320. The information from the MRN can be translated into a medication and medication for the patient's medication list by the electronic medical record database.

The medication(s) and medication information associated with the MRN are communicated from the electronic medical record database to the prescription reminder manager which receives and loads the prescription information for the MRN to the user device at step 325. Multiple MRNs may be entered by the user and the associated information is communicated back to the user device for each of the MRNs.

Consumer requests the prescription reminder manager application set a reminder for one or more of the medications at step 330. The reminder(s) are generated by the prescription reminder manager application and are communicated to the Alarm Manager component of the user device at step 335. At the appropriate time, the Alarm Manager component notifies the prescription reminder manager application of the reminder and the prescription reminder manager application displays the reminder to the user via the user device at step 340. The user acknowledges whether the medication has been taken or skipped by selecting the appropriate icon on the user device and this is logged by the prescription reminder manager application at step 345. If the user does not acknowledge the reminder, in one embodiment, the prescription reminder manager application logs the reminder as 'skipped' and/or 'not acknowledged' at step 345. In some embodiments, the user can make changes to the log of the medication if they have forgotten to acknowledge that a medication has been taken.

FIGS. 4-19, as described in more detail below, show embodiments of the present invention including the functionality and user interaction with display screens.

Figure 4:
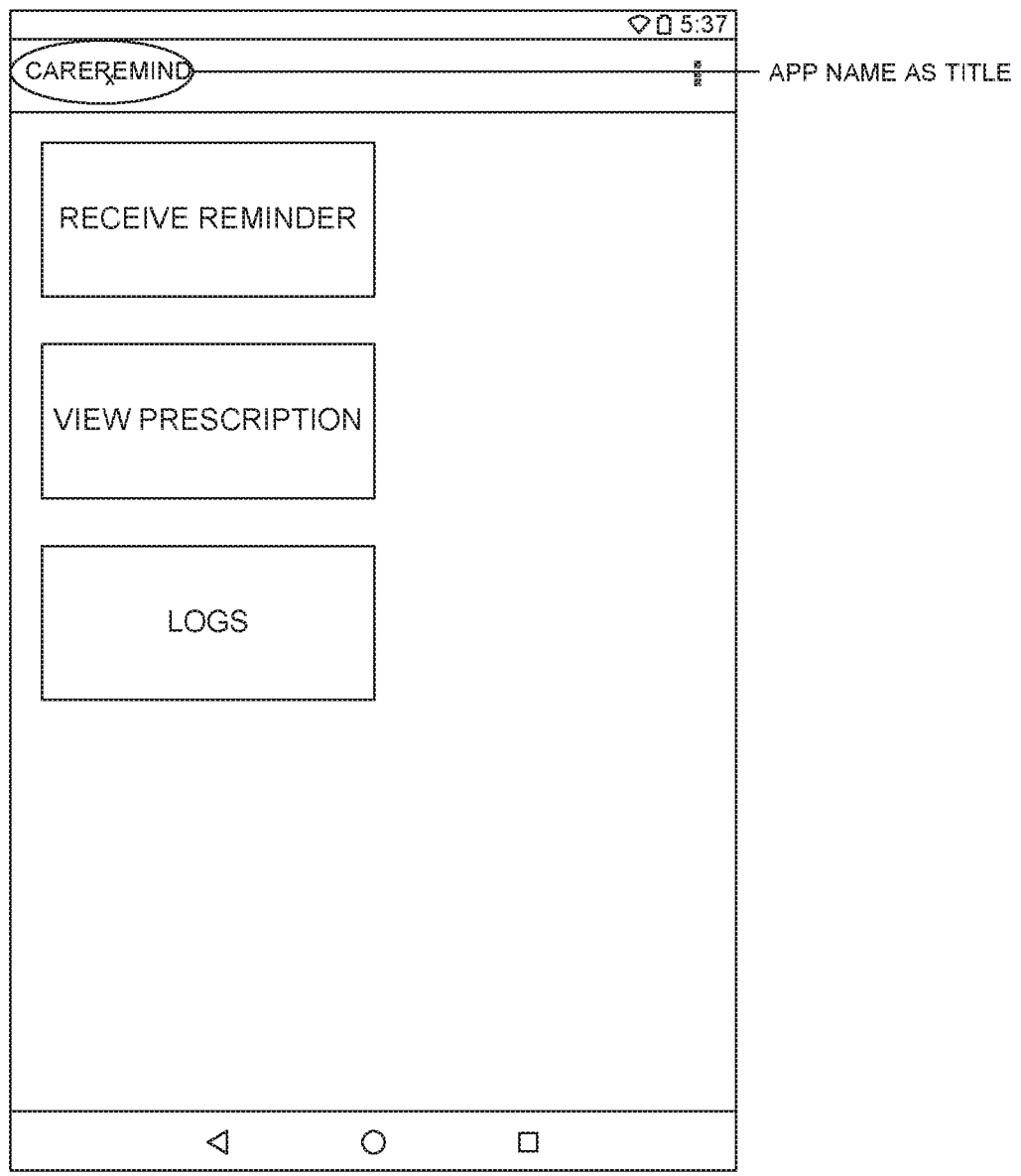

FIG. 4 illustrates the medication reminder screen (CareRemind) home screen. There are three different types of actions that the user can take by interacting with the home screen of FIG. 4 including: (1) receiving a reminder (2) viewing a prescription and (3) viewing logs.

Figure 5:
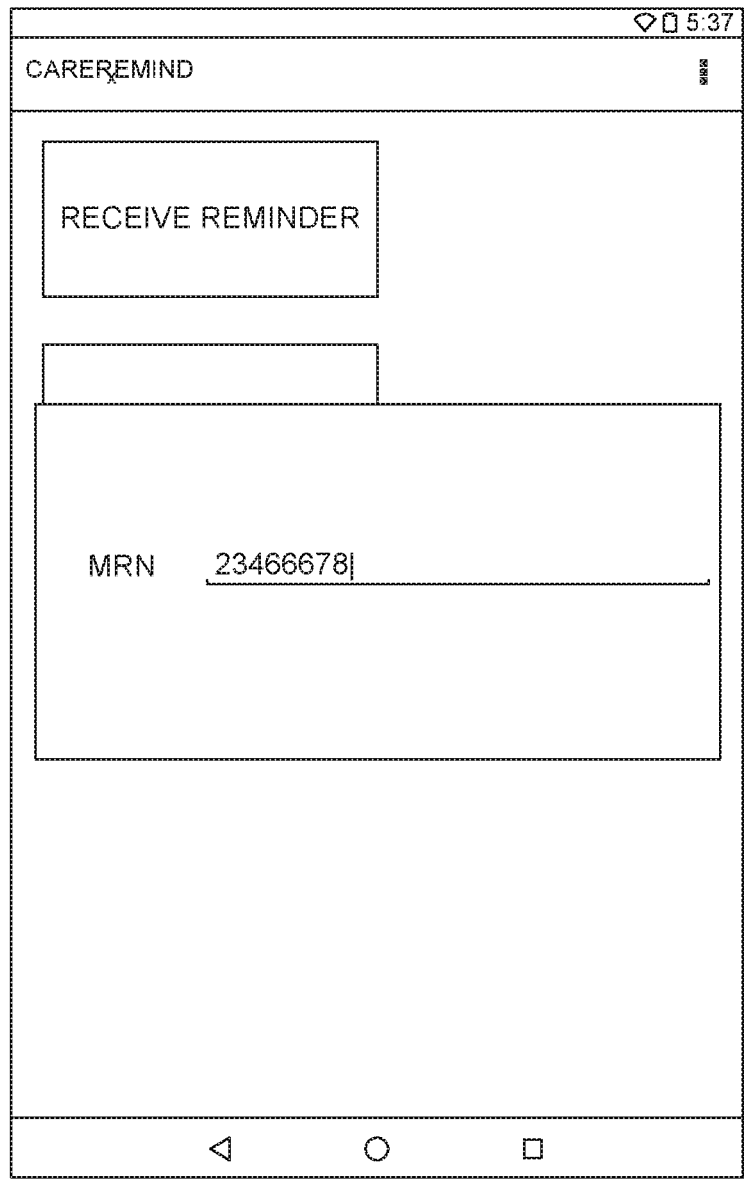

Upon a user selecting choosing the 'Receive Reminder' action from a touch screen or by clicking on an icon, a screen as shown in FIG. 5 is displayed in which the user can input his/her MRN (Medical Record Number) and click on submit button to send request from the consumer device to the electronic medical record database such as the Cerner Millennium database. The submit button is enabled when MRN field is provided with value.

Figure 6:
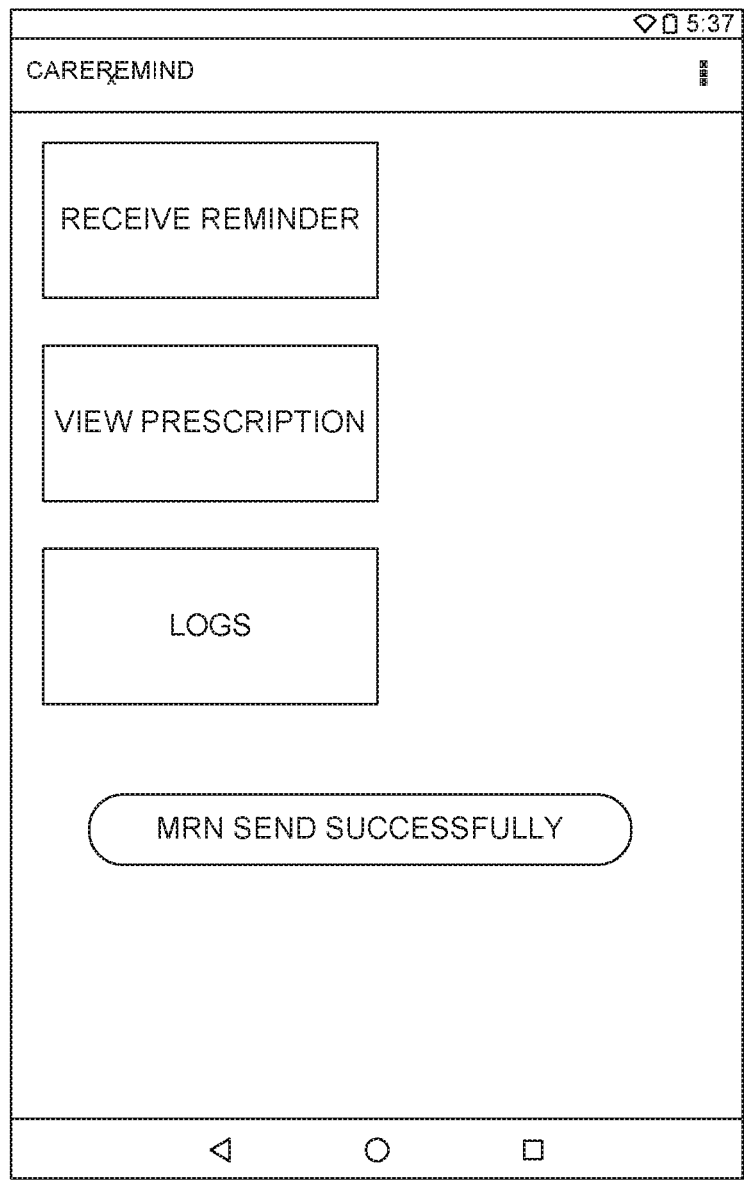

After the user inputs the MRN and submits, a message 'MRN Send Successfully' is displayed to user is displayed in FIG. 6 on the consumer device indicating that the request was successfully from the mobile device to the electronic medical record database.

Figure 7:
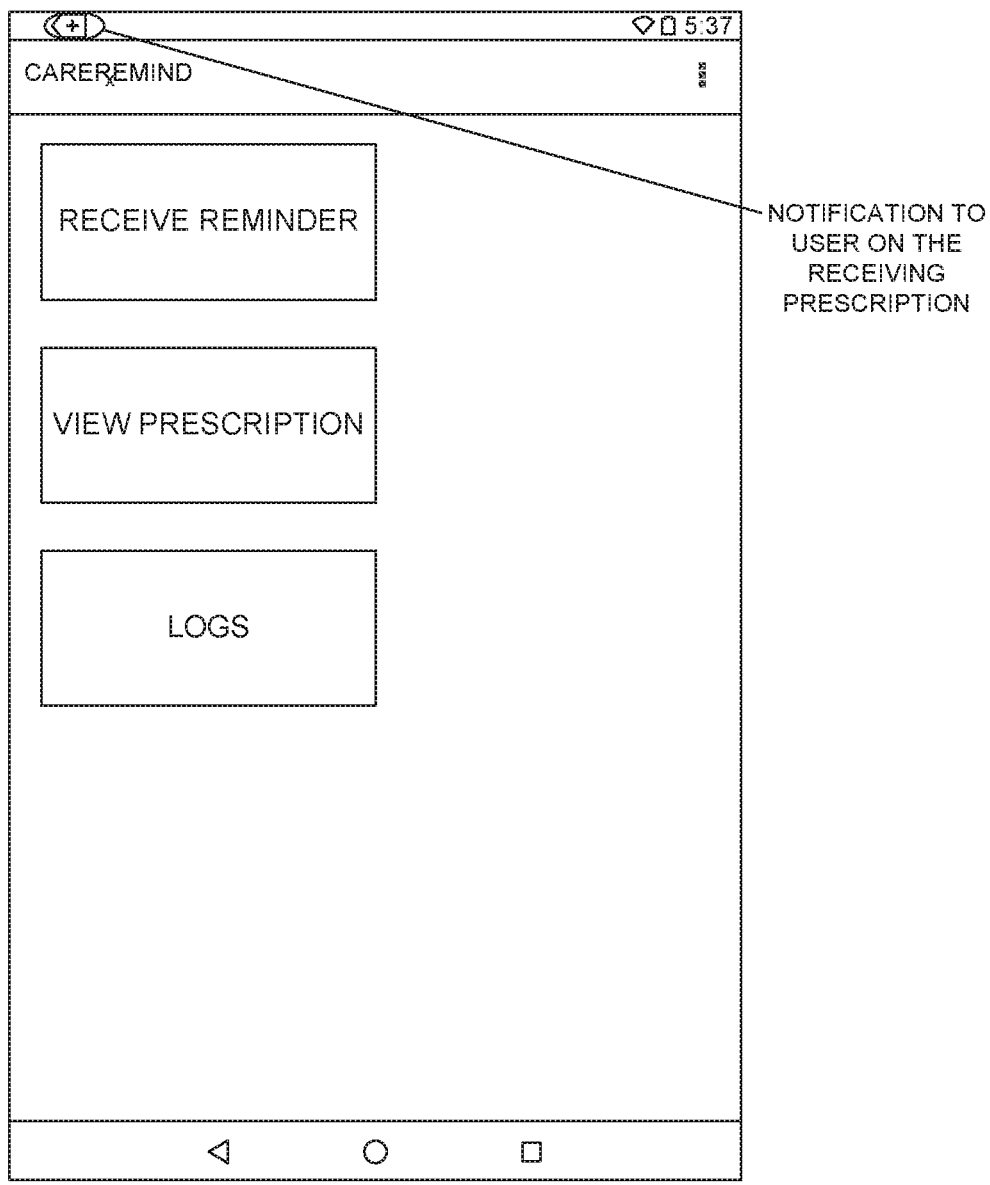

Upon receiving latest prescription as response from the electronic medical record database to the mobile device, the user is notified with an icon being displayed in the notification bar on top of the mobile device screen as shown in FIG. 7. In this embodiment, the notification is depicted as a "+" in the upper left corner but it will be appreciated that any notification mechanism may be displayed in any location.

Figure 8:
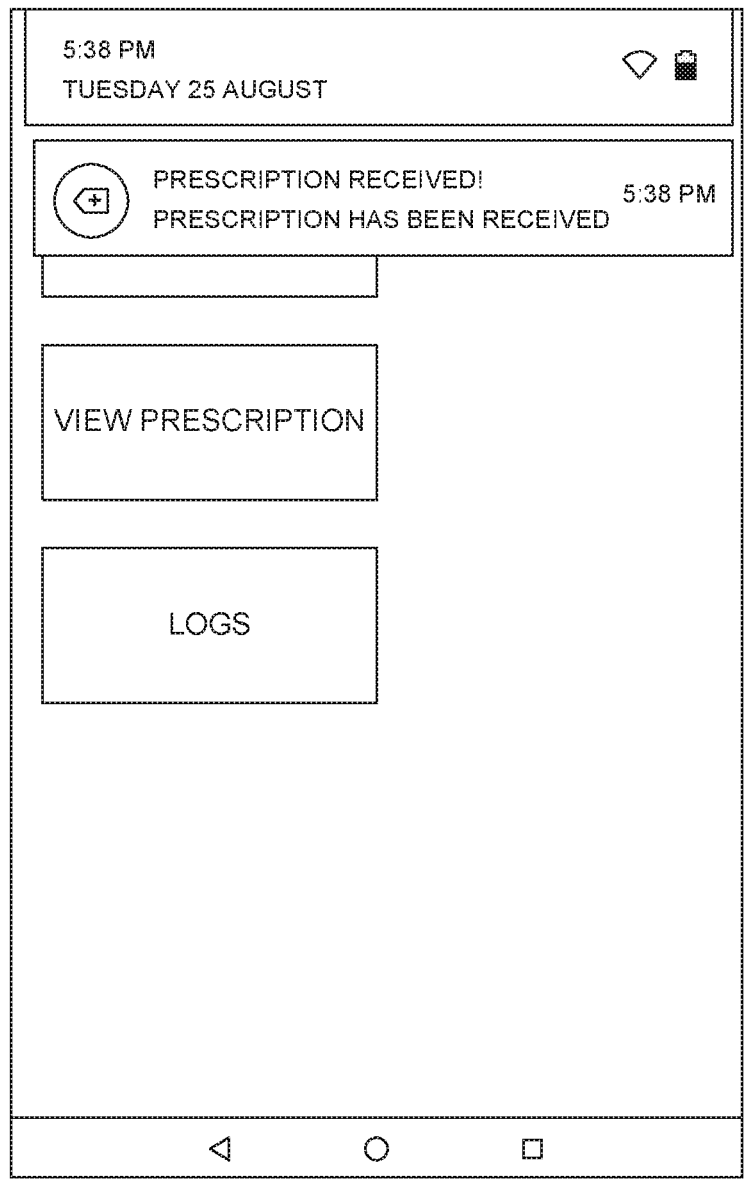

On the user's selection of the icon in the notification bar either by touch or clicking on the icon, the icon along with the message and time (i.e., time when the message was received) is displayed as shown in FIG. 8. The 'Prescription' screen can be opened by the user by clicking on the message "Prescription Received!" shown in FIG. 8. Alternatively, the 'Prescription' screen can be accessed by the user selecting the 'View Prescription' action button from the home page as shown in FIG. 4.

Figure 9:
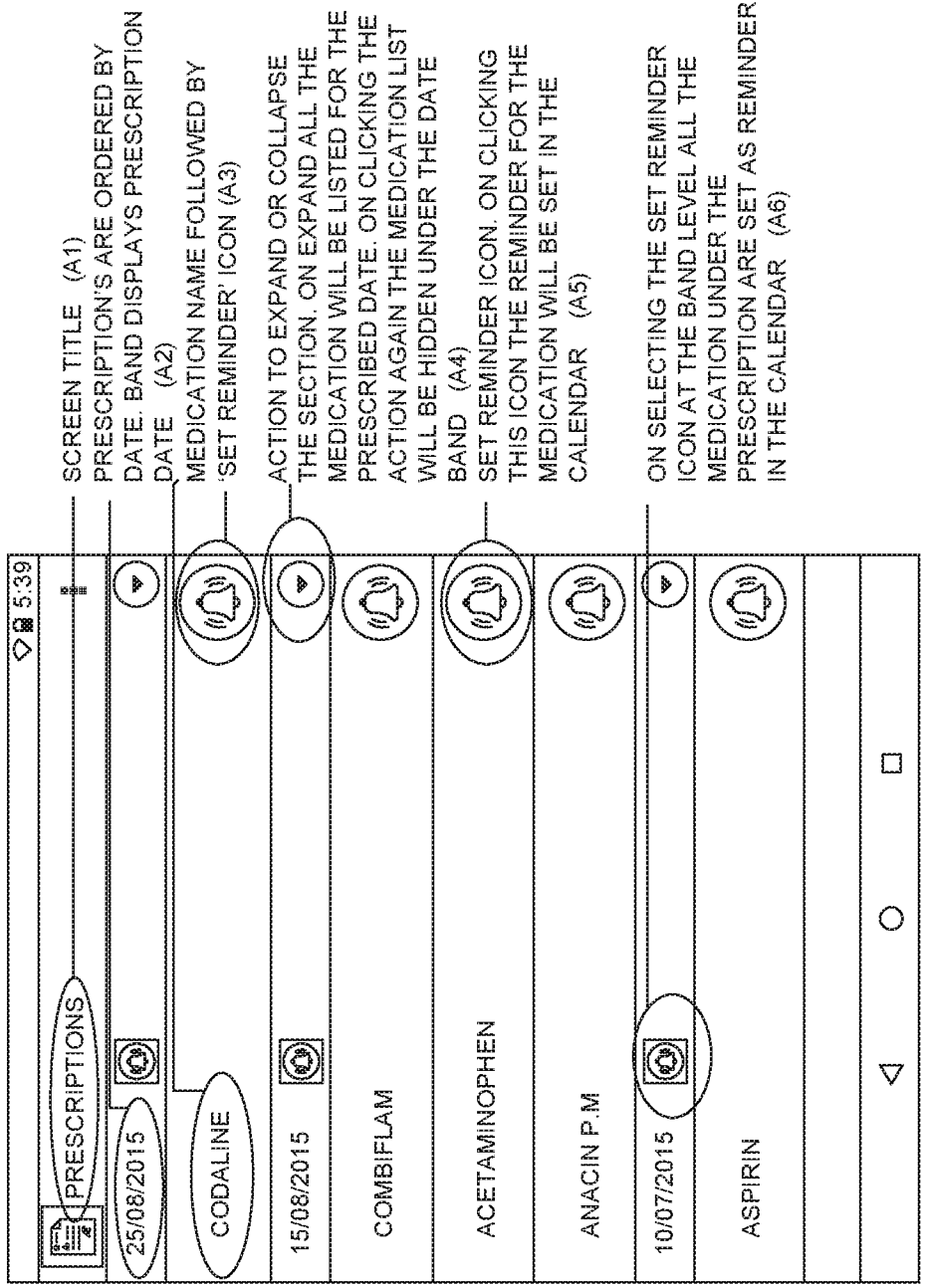

Referring next to FIG. 9, the display of the prescriptions for the user associated with the input MRN are displayed on the mobile device screen and in this embodiment, are displayed in a band for each prescription order date. The prescriptions are ordered in the display in descending order, e.g., the most recent prescription is at the top of the list. Prescriptions that have not expired for the patient are listed on the screen. Notifications as shown in FIG. 8, are displayed when the MRN is entered and sent as a request to the electronic medical record database. The user will not typically receive multiple notifications for a single MRN using this application.

Figure 10:
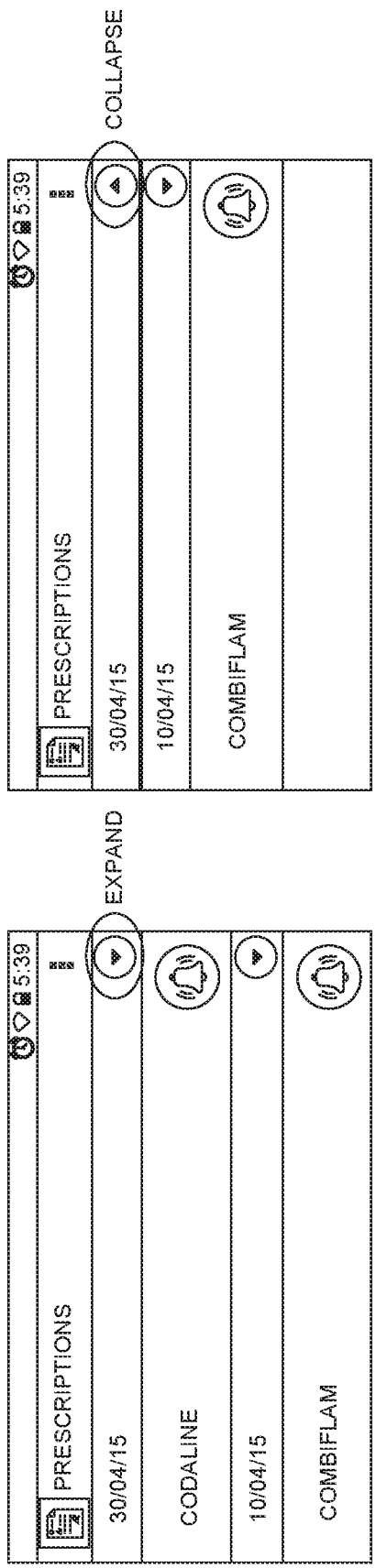
Figure 11:
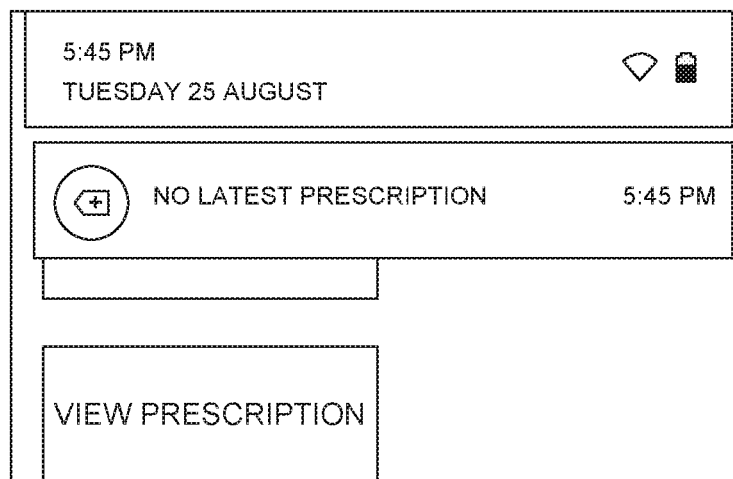

In FIG. 9, the patient has prescription bands for Aug. 25, 2015, Aug. 15, 2015 and Oct. 7, 2015. The band can be selected to expand or collapse the viewing list of items prescribed on that date as shown in FIG. 10. An icon for "set reminder" is displayed next to each prescription name and at each band level.

A user can select to set reminders for individual prescriptions listed. For example, in FIG. 9, the user may select to set a reminder for an individual prescription by selecting the "set reminder" icon displayed next to the name of the prescription. Alternatively, the user may select the "set reminder" icon at the band level for all prescriptions ordered on the date of the band (e.g., for the MRN entered). For example, the user can select the set reminder icon for all prescriptions ordered on Jul. 10, 2015 at the band level.

The selection of the "set reminder" icon for a particular prescription or at the band level sets a reminder in the Alarm Manager component of the mobile device. Reminder setting for prescriptions and at the band level is discussed in more detail below with reference to FIGS. 13 and 14. Expired prescriptions are removed from prescription list displayed in FIG. 9, upon expiration or the stop/end date for administering the medication.

Referring next to FIG. 12, the user may view more detailed information for each prescription in the prescription list. This is done by a long press or selection of the user on the prescription list of FIG. 9. FIG. 12 depicts the screen with detailed information for a prescription medication. If the user wishes to return to the prescription list screen of FIG. 9, the user selects the back button shown on the bottom left of FIG. 12. The detailed information for the prescription includes strength dose, dose unit, drug form, administration route, frequency and descriptions and instructions as shown in FIG. 12. Additional information for the prescription may also be displayed including pharmacy information such as name and phone number, a button to refill the medication, refill reminders, warnings and instructions for the patient included in the prescription (e.g., take with food, do not mix with alcohol).

Figures 13, 14:
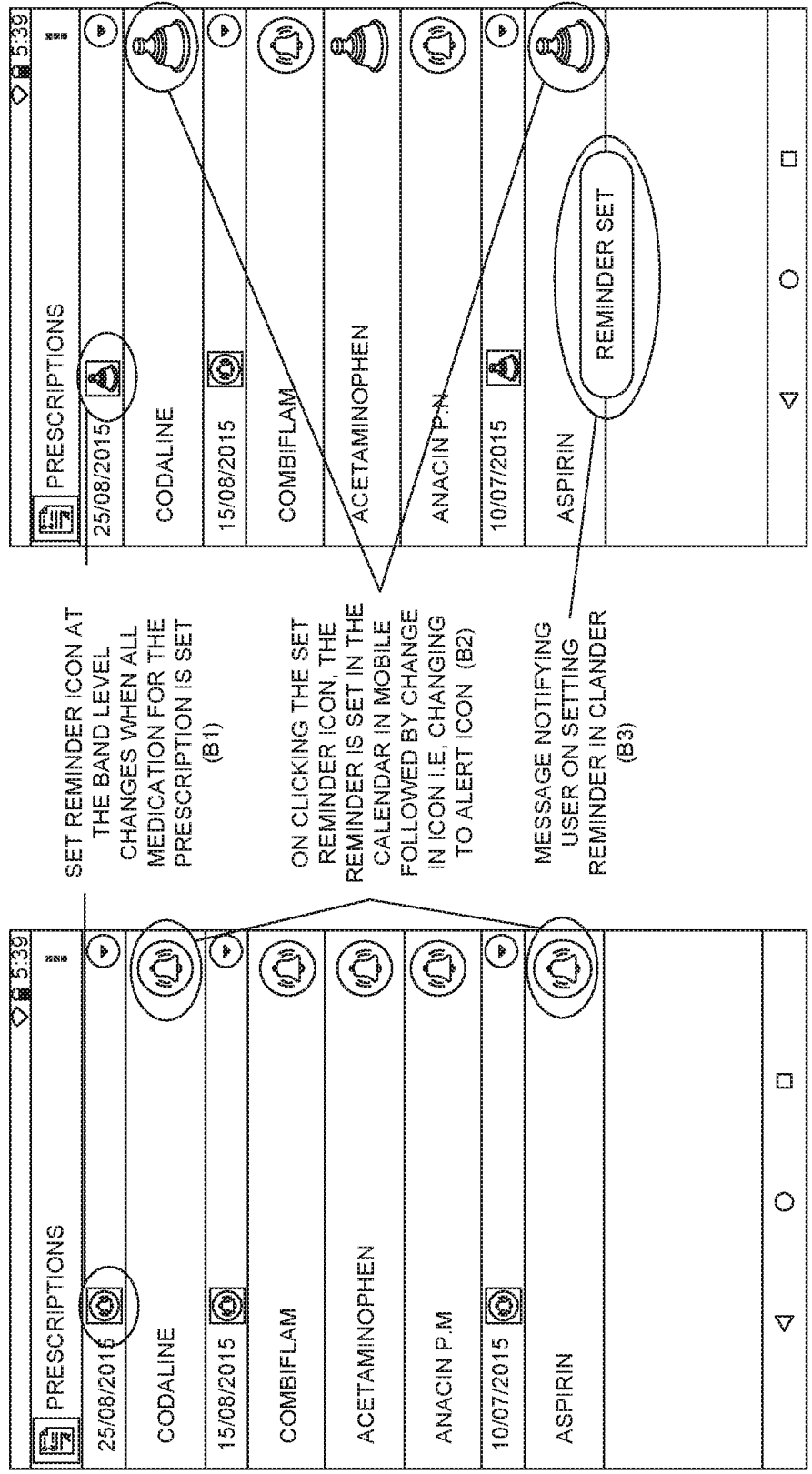

Referring next to FIGS. 13 and 14, reminders for medications can be set by the user two ways. First, the user can set a reminder for all medication prescriptions at the band level by selecting the 'Set Reminder' icon at the band level as shown in the screen design above for the prescription dated 25 Aug. 2015 and Oct. 7, 2015. Upon selection, the icon at the band level changes from 'Set Reminder' to 'Alert' at the band level when all the medications under the prescriptions are set as reminder as shown with reference to the prescription band level dated Aug. 25, 2015 in FIG. 13 and FIG. 14. In addition, the icon for each of the medications under the band level is changed from the 'Set Reminder' icon to the 'Alert' icon. In addition a reminder is set in the Alarm Manager component of the user device for each of the respective medications from its start date/time to end date/time and a notification "reminder set" message is displayed to indicate that the reminder has been set for the user. If the entire band level is not set for reminder, the icon at the band level does not change at the band level for example for the prescription band level dated Aug. 15, 2015.

The user can set a reminder for individual medication instead of at the band level by selecting the 'Set Reminder' icon at the medication level as shown in the screen design of FIGS. 13 and 14 for the medication acetaminophen for in the prescription band level for Aug. 15, 2015. Upon selection, the icon at the medication level changes from 'Set Reminder' to 'Alert' at the medication level as shown with reference to the medication acetaminophen dated Aug. 15, 2015 in FIG. 13 and FIG. 14. In addition a reminder is set in the Alarm Manager component of the user device for the medication from its start date/time to end date/time and a notification "reminder set" message is displayed to indicate that the reminder has been set for the user.

Figure 16:
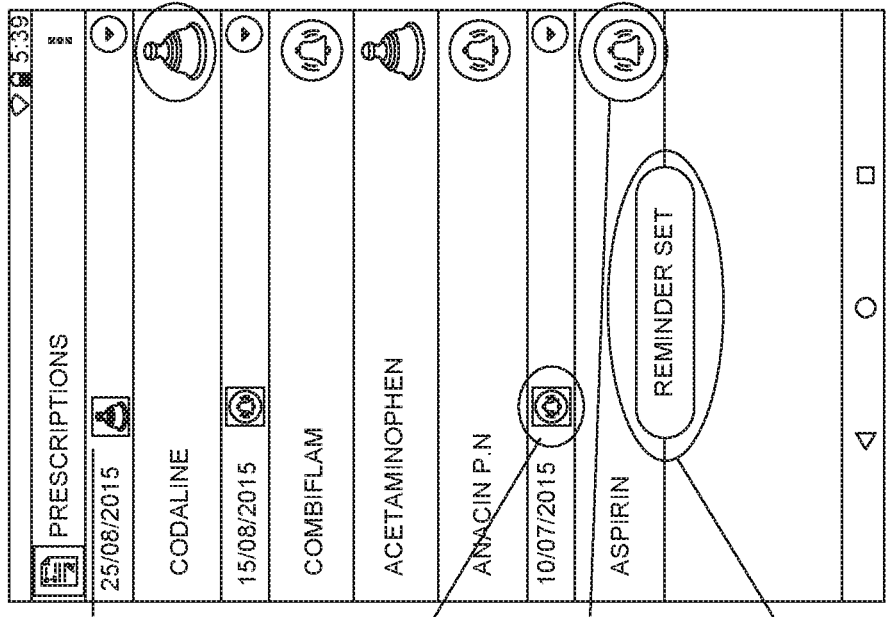
Figure 15:
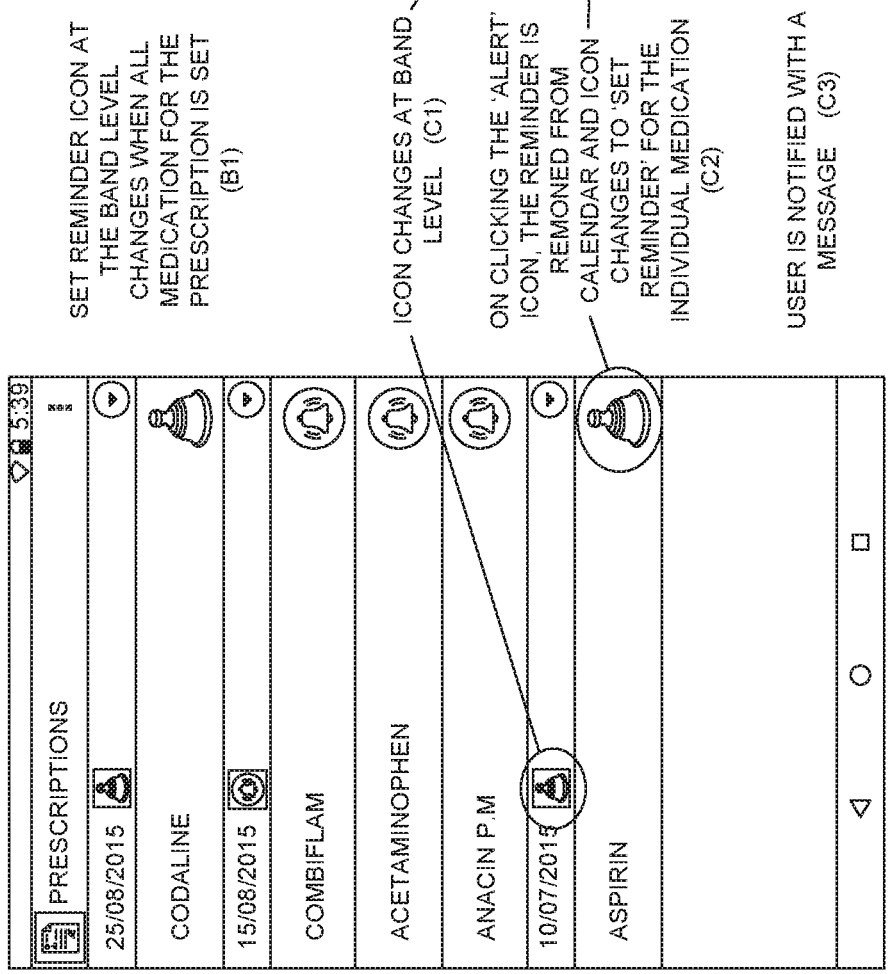

Referring next to FIGS. 15 and 16, the user has the ability to remove reminders from the Alarm Manager component. First, once the reminder is set at the band level, the user selects or clicks on the 'Alert' icon again at band level, all the reminders will be removed from Alarm Manager component for medications at a time (for the given prescription band level). The icon then changes back to 'Set Reminder' icon at the band level and for each of the medications as shown in FIGS. 15 and 16.

For reminders set for individual medications, the reminder can be removed from the Alarm Manager component for the individual medications by selecting or click on the 'Alert' icon again the reminder for individual medications. The icon for the medication then changes back to 'Set Reminder' icon. If all reminders for medications individually are removed, the respective prescription icon changes from the 'Alert' icon to the 'Set Reminder' icon at the band level as shown in FIGS. 15 and 16. Additional, the user is notified on removing the reminder from the Alarm Manager component as shown in FIG. 16.

Figure 17:
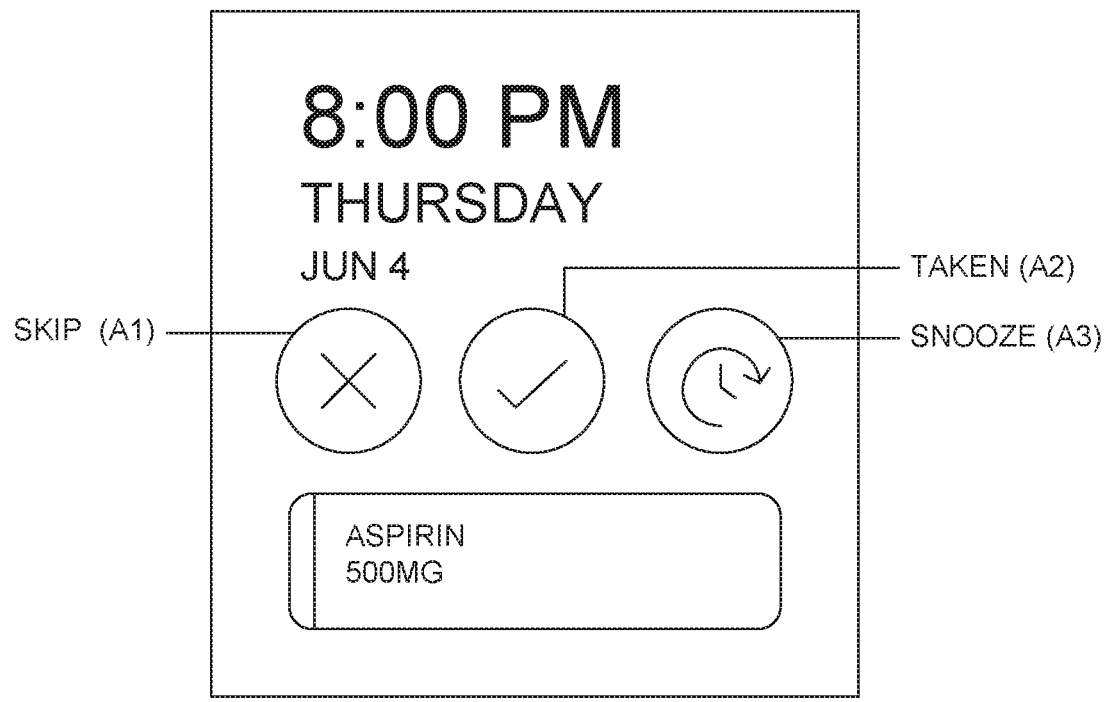

Referring next to FIG. 17, medication reminders are set leveraging the Alarm Manager component of a mobile device, such as a smart phone or android device. As discussed above, the prescription reminder manager uses the Alarm Manager component available within the mobile device to receive notifications about alerts. For example, there is a reminder set on the Alarm Manager component to alert user at LOAM for Aspirin the prescription reminder manager will receive this alert from the Alarm Manager component. On receipt of this alert, the prescription reminder manager will update the status bar of mobile device. User touches the notification take further action.

FIG. 17 is a representation a medication reminder screen (medication reminder screen). The medication reminder screen is displayed on the user device when the user touches or selects the notification icon in the notification bar of the mobile (as shown in FIG. 7).

The medication reminder screen as shown in FIG. 17 displays the following information:

Time Followed by Day and Date

Skip icon that can be selected by user to skip the medication

Taken icon that is selected by user to acknowledge the medication as taken

Snooze icon that is selected by user to postpone the reminder by selecting the snooze time. The reminder will be displayed to user after the snooze time. The user can select the snooze time in different increments such as 5/15/30/45/60 minutes.

Medication Name Followed by Dose

Figure 18:
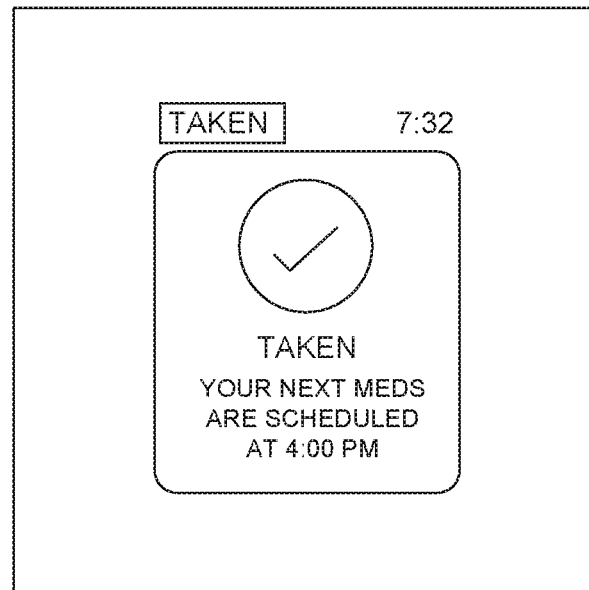

Referring next to FIG. 18, an Action Summary Window is shown. The Action Summary Window displays a summary of the action that has been taken on the medication reminder screen. FIG. 17 displays the summary when a user clicks/touches the Taken button in the medication reminder screen. The acknowledged reminders (i.e., reminder marked as taken or skipped) are stored as logs in the mobile database of the medication reminder manager which are discussed with more detail below with reference to FIG. 18.

Figure 19:
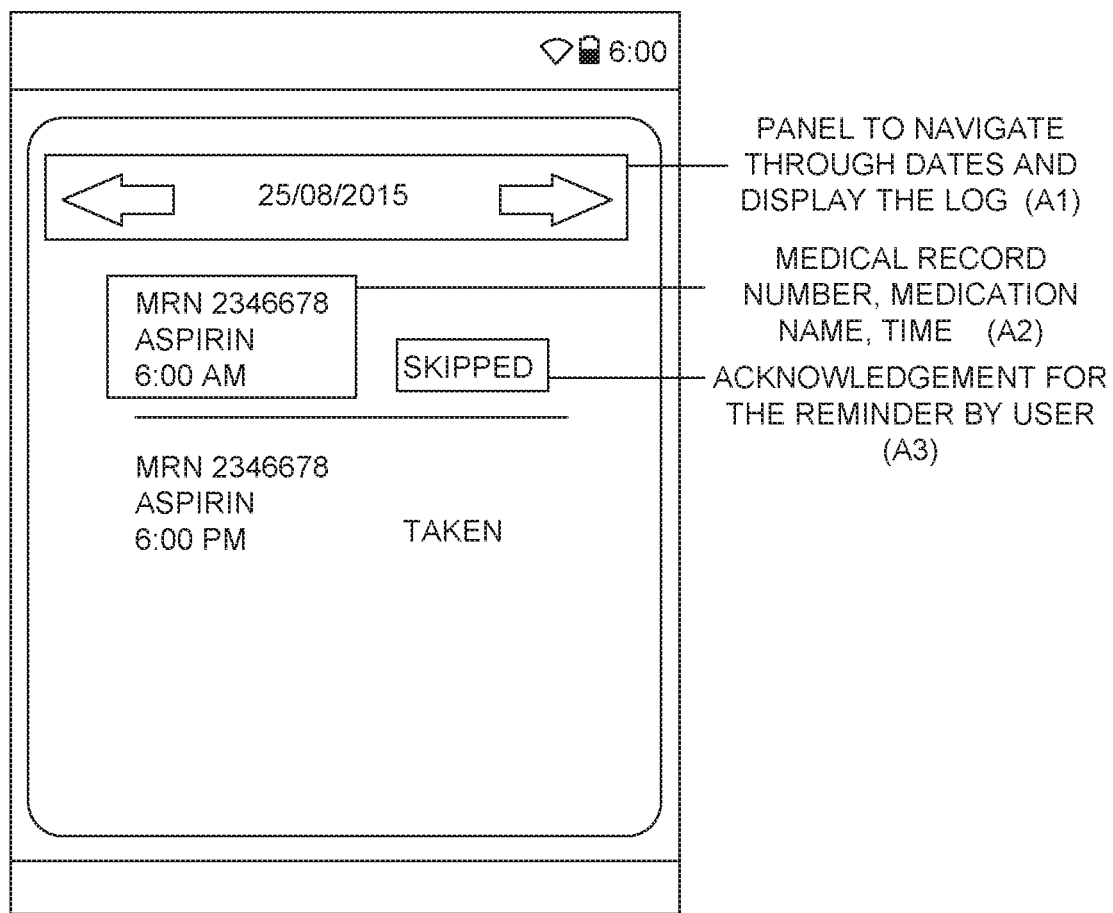

FIG. 19 displays to the user current log information. The user can navigate through dates using the navigation buttons to navigate dates backward and forward. The information is displayed in the log includes date of prescription, the MRN, followed by medication name followed by time when the notification was acknowledge as taken or skipped.

Each schedule dose of medication for each medication is listed as log after user acknowledges the notification as taken or skipped. User can download or electronically transfer the logged information as they see fit to give to their clinician, pharmacy or caregiver as a record of their medication compliance/non-compliance.

The present invention has been described in relation to particular embodiments, which are intended in all respects to be illustrative rather than restrictive. Further, the present invention is not limited to these embodiments, but variations and modifications may be made without departing from the scope of the present invention.

The invention claimed is:

1. A system comprising:
one or more computer processors on an individual's computing device programmed to:
receiving from an individual's electronic medical record, identification of one or more medications and a reminder time and date for the one or more medications in response to the individual's computing device communicating a medical record number to an electronic medical record service;
generating and presenting, via the individual's computing device, an interactive screen that simultaneously presents the one or more medications, a reminder icon, and the reminder time and date for the one or more medications;
in response to receiving a selection of the reminder icon presented on the interactive screen, requesting to set a medication reminder on the individual's computing device, wherein the medication reminder is an indication for an individual to take the one or more medications;
when the requested medication reminder is set, automatically communicating the reminder time and date to an alarm manager component of the individual's computing device;
subsequent to communicating the reminder time and date to the alarm manager component, automatically at the reminder time and date receiving from the alarm manager component an indication to present the medication reminder;
presenting the medication reminder on the interactive screen on the individual's computing device in response to the indication received from the alarm manager component; and
in response to receiving a selection of the reminder icon on the interactive screen, automatically changing the reminder icon to an alert icon as presented on the interactive screen, wherein the alert icon is selectable to remove the corresponding medication reminder.

2. The system of claim 1, further comprising presenting simultaneously on the interactive screen a skip icon simultaneously with the medication reminder, wherein the skip icon indicates the one or more medications have been skipped.

3. The system of claim 2, further comprising receiving from the interactive screen a selection of the skip icon indicating the one or more medications have been skipped.

4. The system of claim 1, further comprising presenting simultaneously on the interactive screen a snooze icon simultaneously with the medication reminder, wherein the snooze icon indicates an increment of time to postpone the medication reminder.

5. The system of claim 4, further comprising:
receiving on the interactive screen a selection of the snooze icon; and
postponing the medication reminder for the increment of time.

6. The system of claim 1, further comprising receiving from the interactive screen an indication the one or more first medications have been taken or skipped.

7. The system of claim 6, further comprising:
creating a first database record for the one or more medications; and
automatically updating the first database record with the indication that the one or more medications have been taken or skipped.

8. The system of claim 1, further comprising receiving from the interactive screen a request to delete the medication reminder for the one or more medications based on a selection of the alert icon.

9. The system of claim 8, further comprising:
creating a first database record for the one or more medications; and
updating the first database record to delete the medication reminder to take the one or more medications.

10. The system of claim 1, simultaneously displaying on the interactive screen the alert icon and the one or more medications and the reminder time and dates for the one or more medications.

11. The system of claim 1, wherein receiving from the patient's electronic medical record further comprises receiving a frequency and a duration for each of the one or more medications.

12. The system of claim 11, further comprising generating the reminder time and date based on the frequency and the duration of the one or more medications.

13. One or more computer storage media having computer-usable instructions that, when used by one or more computing devices, cause the one or more computing devices to perform a method serving medication reminders to a patient, the method comprising:
receiving, from an individual's medical record, identification of one or more medications and a reminder time and date for the one or more medications in response to the individual's computing device communicating a medical record number to an electronic medical record service;
generating and presenting, via the individual's computing device, an interactive screen that simultaneously presents the one or more medications, a reminder icon, and the reminder time and date for the one or more medications;
in response to receiving a selection of the reminder icon presented on the interactive screen, requesting to set a medication reminder on the individual's computing device, wherein the medication reminder is an indication for an individual to take the one or more medications;
when the requested medication reminder is set, automatically communicating the reminder time and date to an alarm manager component of the individual's computing device;
subsequent to communicating the reminder time and date to the alarm manager component, automatically at the reminder time and date receiving from the alarm manager component an indication to present the medication reminder;
presenting the medication reminder on the interactive screen on the individual's computing device in response to the indication received from the alarm manager component; and
in response to receiving a selection of the reminder icon on the interactive screen, automatically changing the reminder icon to an alert icon as presented on the interactive screen, wherein the alert icon is selectable to remove the corresponding medication reminder.

14. The media of claim 13, further comprising:
receiving from the interactive screen an indication the one or more first medications have been taken or skipped.

15. The media of claim 14, further comprising:
creating a first database record for the one or more medications; and
automatically updating the first database record with the indication that the one or more medications have been taken or skipped.

16. The media of claim 13, further comprising:
receiving from the interactive screen a request to delete the medication reminder for the one or more medications based on a selection of the alert icon.

17. The media of claim 16, further comprising:
creating a first database record for the one or more medications; and
updating the first database record to delete the medication reminder.

18. The media of claim 13, wherein receiving from the patient's electronic medical record further comprises receiving a frequency and a duration for each of the one or more medications.

19. The system of claim 18, further comprising generating the reminder time and date based on the frequency and duration of the one or more medications.

20. The media of claim 13, simultaneously displaying on the interactive screen the alert icon and the one or more medications and the reminder time and dates for the one or more medications.

* * * * *